US00PP36483P3

(12) United States Plant Patent
Olesen

(10) Patent No.: US PP36,483 P3
(45) Date of Patent: Feb. 25, 2025

(54) ROSE PLANT NAMED 'POULPAH120'

(50) Latin Name: *Rosa hybrida*
Varietal Denomination: Poulpah120

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/445,475

(22) Filed: Sep. 8, 2023

(65) Prior Publication Data

US 2024/0107914 P1 Mar. 28, 2024

(30) Foreign Application Priority Data

Sep. 30, 2022 (QZ) ..... PBR 2022/2167

(51) Int. Cl.
*A01H 5/02* (2018.01)
*A01H 6/74* (2018.01)

(52) U.S. Cl.
USPC ..... Plt./117
CPC ..... *A01H 6/749* (2018.05)

(58) Field of Classification Search
USPC ..... Plt./117
CPC ..... A01H 6/749; A01H 5/02
See application file for complete search history.

*Primary Examiner* — Keith O. Robinson

(57) ABSTRACT

A new garden rose plant of the miniature class which has abundant, white flowers and attractive foliage. This new and distinct variety has shown to be uniform and stable in the resulting generations from asexual propagation.

2 Drawing Sheets

Botanical designation: *Rosa hybrida.*

Variety denomination: 'Poulpah120'.

This application claims priority to Plant Breeder's Rights Application Number 2022/2167, which was filed at the Community Plant Variety Rights Office in the European Union on Sep. 30, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulpah120', originated as a single seedling from the stated cross.

The new variety may be distinguished from its male pollen parent and female seed parent primarily by the following characteristics. The male pollen parent plant has white flowers with about 50 petals while the new variety has white flowers with about 95 petals. The female seed parent plant grows to a mature height of 100 cm, while the new variety grows to 50 cm.

The objective of the hybridization of this rose variety was to create a new and distinct variety with unique qualities, such as:

1. Uniform and abundant white flowers;
2. Vigorous, but compact growth when propagated on its own roots;
3. Exceptional disease resistance.

This combination of qualities is not present in previously available commercial cultivars of this type, known to the inventor, and distinguish 'Poulpah120' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulpah120' was selected in the spring of 2016 by the inventor as a single plant from the progeny of the aforementioned hybridization.

Asexual reproduction of 'Poulpah120' by rooted cuttings was first done by Mogens N. Olesen in the nursery in Fredensborg, Denmark in July 2016. This initial and other subsequent asexual propagations conducted in controlled environments have demonstrated that the characteristics of 'Poulpah120' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah120'.

Specifically illustrated in FIG. 1 of the drawings are flowers at various stages of opening viewed from above and the side, sepals detached revealing reproductive flower parts, flower petals detached, and a flower bud showing expression of anthocyanin.

Figure 1:
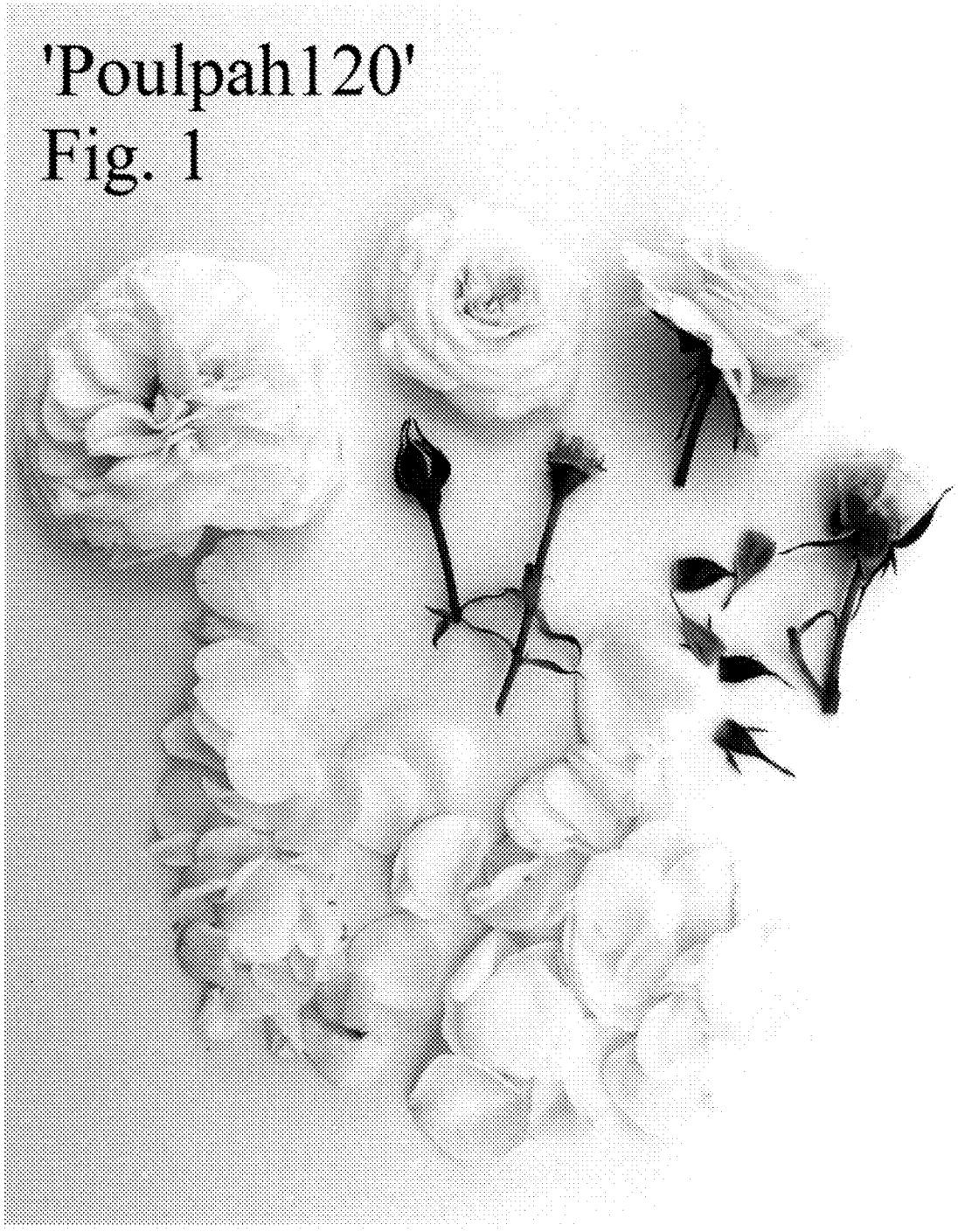
Figure 2:
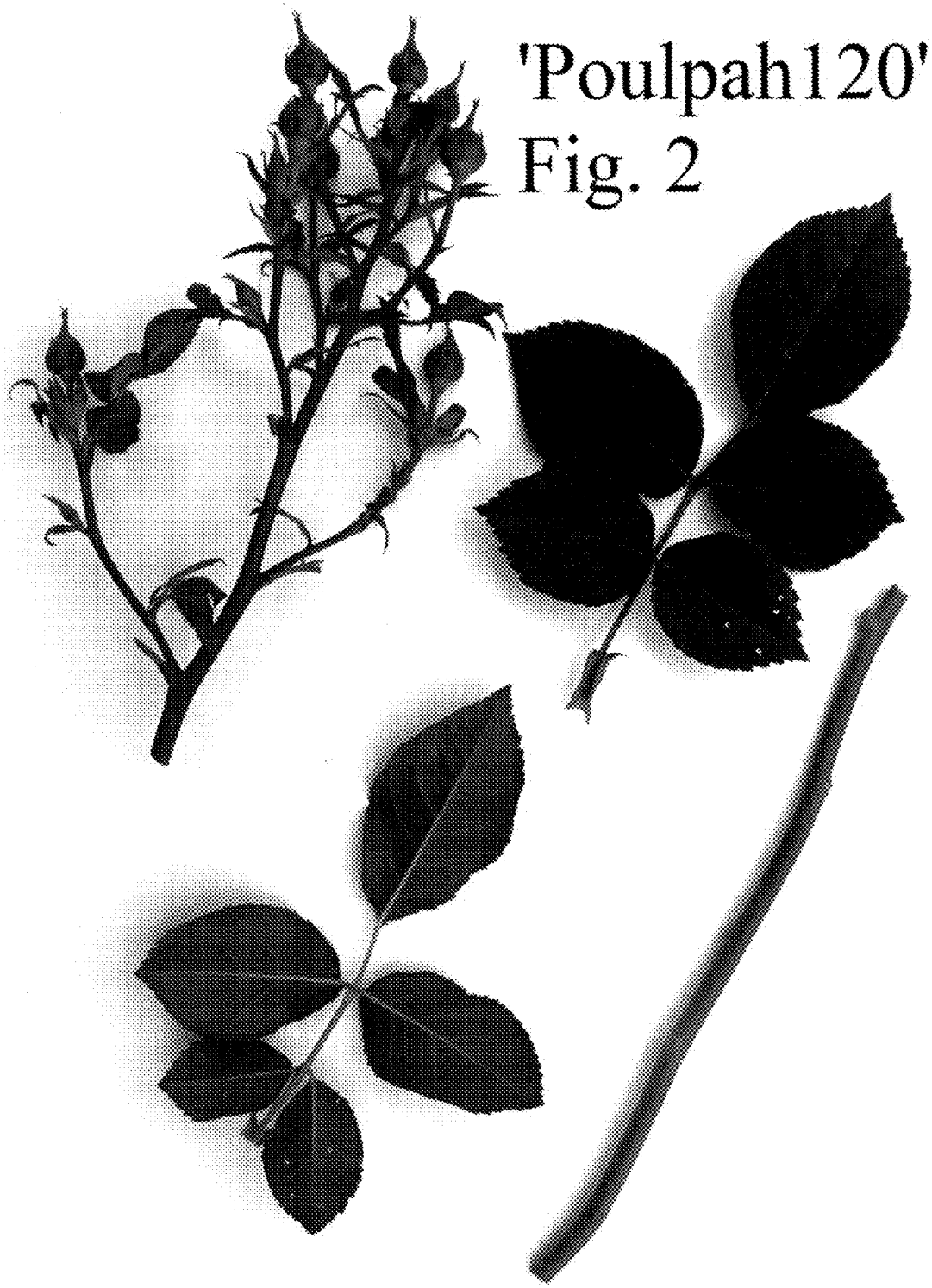

Specifically illustrated in FIG. 2 of the drawings are a cluster of flower buds on a branch showing the inflorescence type and number of flower buds produced on a branch, a bare stem exhibiting prickles, and mature leaves. Plants shown are 1 year old.

DETAILED DESCRIPTION OF THE VARIETY

The following is a description of 'Poulpah120', as observed in its growth in an outdoor nursery in Odense Denmark. Observed plants are 12 months of age, and were grown on their own roots in 24 cm pots. Color references are made using The Royal Horticultural Society (London, England) Colour Chart, 2001, except where common terms of color are used.

For a comparison, several physical characteristics of the rose variety 'Poulpah104', U.S. Plant Pat. No. 33,199 are compared to the claimed plant. While 'Poulpah120' has 95 flower petals, 'Poulpah104' has 75 to 80 flower petals. The claimed plant has a flower diameter of 90 mm while 'Poulpah104' has a flower diameter of 60 mm. The claimed plant has slightly larger flower petals, 43 mm (l)×41 mm (w), while 'Poulpah104' has flower petals about 34 mm (l)×34 mm (w).

FLOWER AND FLOWER BUD

Blooming habit: Continuous.

Flower bud:

- *Size*.—Upon opening, 20 mm in length from base of receptacle to end of bud. Bud diameter is 15 mm.
- *Bud form*.—Urceolate.
- *Bud color*.—Red Group 46B.
- *Sepal inner surface*.—Color: Yellow-Green Group 146D. Surface: Lightly pubescent.
- *Sepal outer surface*.—Color: Yellow-Green Group 144A with intonations of Greyed-Purple Group 187B. Texture: Smooth.
- *Sepal shape*.—Apex: Cirrhose. Base: Flat at union with receptacle.
- *Sepal margin*.—Margins have moderate foliaceous appendages on three of the five sepals.
- *Sepal size*.—25 mm long, 7 mm wide.
- *Receptacle*.—Texture: Smooth. Size: 6 mm in height, 6 mm wide. Color: Yellow-Green Group 144A with intonations of Greyed-Purple Group 187C. Shape: Campanulate.
- *Pedicel*.—Surface: Smooth. Length: 35 mm. Diameter: 3 mm on average. Color: Yellow-Green Group 144A with intonations of Greyed-Red Group 180A. Strength: Strong.
- *Peduncle*.—Length: 4 to 5 cm. Diameter: About 3 mm. Color: Yellow-Green Group 146B with strong intonations of Greyed-Purple Group 184A. Texture: Smooth.

Flower bud development: Flower buds are borne in clusters of 15 flower buds per stem. Development as a panicle.

Flower bloom:

- *Fragrance*.—Light to moderate floral scent.
- *Duration*.—The blooms have a duration on the plant of approximately 21 days. Petals fall cleanly away from plant after flowers have fully matured.
- *Size*.—Flower diameter is 90 mm when open. Flower depth is 30 mm.
- *Flower shape*.—Quartered-rosette, very double, with many overlapping petals packed into quarter sections.
- *Shape of flower, side view*.—The upper portion is flat. The lower portion is flat convex.

Petalage: Under normal conditions, flowers have about 95 petals.

General tonality of flower: Open flowers are White Group 155B with intonations of Yellow Group 8D.

Petal color:

- *Upon opening, outer petals*.—Upper surface: White Group 155B. At the basal zone Yellow Group 4D. Lower surface: White Group 155B. At the basal zone Yellow Group 4D.
- *Upon opening, inner petals*.—Upper surface: Yellow Group 8D. Lower surface: Yellow Group 8D.
- *After opening, outer petals*.—Upper surface: Green-White Group 157D at the middle and basal zone. Marginal zone White Group 155B. Lower surface: Green-White Group 157D at the middle and basal zone. Marginal zone White Group 155B.
- *After opening, inner petals*.—Upper surface: Yellow Group 8D. Lower surface: Yellow Group 8D.

Petals:

- *Petal reflex*.—Partially reflexed.
- *Margin*.—Entire and uniform. Moderate undulations.
- *Shape*.—Broad and elliptic. Apex shape: Rounded. Base shape: Acute.
- *Size*.—43 mm (l)×41 mm (w).
- *Texture*.—Smooth.
- *Thickness*.—Average.

Petaloids:

- *Size*.—10 mm (l) by 5 mm (w).
- *Quantity*.—About 30.
- *Shape*.—Elliptical with an acute base and rounded apices.
- *Color*.—Yellow Group 8D on the upper and lower surface.

Reproductive flower parts:

- *Pollen*.—None observed.
- *Anthers*.—Size: 2 mm in length. Color: Greyed-Yellow Group 162A. Quantity: 46 on average.
- *Filaments*.—Color: Green Yellow 1D. Length: 4 mm.
- *Pistils*.—Length: 8 mm. Quantity: 35 on average.
- *Stigmas*.—Color: Green White Group 157A.
- *Styles*.—Color: Green White Group 157A.
- *Location of stigmas*.—Superior in location relative to the length of the filaments and the height of the anthers.
- *Hips*.—None Observed.

PLANT

Plant growth: Upright and well branched. Plants are 50 cm in height, and 45 cm wide.

Stems:

- *Color of juvenile growth*.—Yellow-Green Group 144B.
- *Color of mature growth*.—Yellow-Green Group 144A with intonations of Greyed-Purple Group 184B.
- *Length*.—Canes are about 25 cm from the base of the plant to the flowering portion.
- *Diameter*.—About 6 mm.
- *Internodes*.—On mature canes about 45 mm between nodes.
- *Surface texture*.—Young wood: Smooth. Older wood: Smooth.

Long prickles: None observed.

Plant foliage:

- *Compound leaf*.—165 mm (l)×125 (w).
- *Quantity*.—2 leaves per 10 cm of stem on average.
- *Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 24 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 42 mm. Diameter: 2 mm. Upper surface color: Greyed-Red Group 180A. Lower surface color: Yellow-Green Group 144A.

*Rachis*.—Length: 50 mm. Upper surface color: Yellow-Green Group 144A with intonations of Greyed-Purple Group 183C. Lower surface color: Yellow-Green Group 144A.

*Leaflet*.—Quantity: Normally 5 leaflets. Margins: Serrated. Size: Terminal leaflets are about 71 mm long, 42 mm wide. Shape: Generally elliptical. Base: Rounded. Apex: Acute. Texture: Smooth. Thickness: Average. Arrangement: Odd pinnate. Venation: Reticulate. Glossiness: Glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah120' substantially as described and illustrated herein.

* * * * *

'Poulpah120'

'Poulpah120'